(12) United States Patent
Grim et al.

(10) Patent No.: US 11,517,294 B2
(45) Date of Patent: Dec. 6, 2022

(54) BIOPSY DEVICES AND METHODS OF USE THEREOF

(71) Applicant: COVIDIEN LP, Mansfield, MA (US)

(72) Inventors: Kasey A. Grim, Boulder, CO (US); Joe D. Sartor, Longmont, CO (US)

(73) Assignee: Covidien LP, Mansfield, MA (US)

( * ) Notice: Subject to any disclaimer, the term of this patent is extended or adjusted under 35 U.S.C. 154(b) by 815 days.

(21) Appl. No.: 16/404,848

(22) Filed: May 7, 2019

(65) Prior Publication Data

US 2020/0352549 A1 Nov. 12, 2020

(51) Int. Cl.
| | | |
|---|---|---|
| *A61B 10/02* | (2006.01) | |
| *A61B 8/00* | (2006.01) | |
| *A61B 10/00* | (2006.01) | |
| *A61B 8/08* | (2006.01) | |
| *A61B 17/34* | (2006.01) | |

(52) U.S. Cl.
CPC ......... *A61B 10/0266* (2013.01); *A61B 8/085* (2013.01); *A61B 8/0825* (2013.01); *A61B 8/4455* (2013.01); *A61B 8/4477* (2013.01); *A61B 8/4494* (2013.01); *A61B 8/463* (2013.01); *A61B 10/0041* (2013.01); *A61B 17/3403* (2013.01); *A61B 10/0233* (2013.01); *A61B 2010/0208* (2013.01); *A61B 2017/3413* (2013.01)

(58) Field of Classification Search
CPC ... A61B 10/0266; A61B 8/0825; A61B 8/085; A61B 8/4455; A61B 8/4477; A61B 8/4494; A61B 8/463; A61B 10/0041; A61B 17/3403; A61B 10/0233; A61B 2010/0208; A61B 2017/3413
See application file for complete search history.

(56) References Cited

U.S. PATENT DOCUMENTS

| | | |
|---|---|---|
| 4,321,551 A | 3/1982 | Bleil et al. |
| 5,320,110 A | 6/1994 | Wang |
| 5,526,822 A | 6/1996 | Burbank et al. |
| 5,598,269 A | 1/1997 | Kitaevich et al. |

(Continued)

FOREIGN PATENT DOCUMENTS

| | | |
|---|---|---|
| CN | 203001001 U | 6/2013 |
| EP | 1932481 A1 | 6/2008 |

(Continued)

OTHER PUBLICATIONS

International Search Report and Written Opinion, dated Jun. 21, 2017, corresponding to International Application No. PCT/US2017/028498; 11 total pages.

(Continued)

*Primary Examiner* — Amanda Lauritzen Moher
*Assistant Examiner* — Brooke Lyn Klein

(57) ABSTRACT

A biopsy device includes an elongated handle body having a proximal end portion and a distal end portion, a needle disposed within the handle body, first and second transducers, and a display. The needle is configured to move between a retracted position and a deployed position. The first and second ultrasound transducers are disposed within the distal end portion of the handle body. The first and second ultrasound transducers are angled relative to one another and define a space therebetween configured for passage of the needle.

18 Claims, 10 Drawing Sheets

(56) References Cited

U.S. PATENT DOCUMENTS

| | | |
|---|---|---|
| 5,660,185 A | 8/1997 | Shmulewitz et al. |
| 5,751,869 A | 5/1998 | Li et al. |
| 5,810,541 A | 9/1998 | Casey et al. |
| 5,810,841 A | 9/1998 | McNeirney et al. |
| 5,855,554 A | 1/1999 | Schneider et al. |
| 5,976,092 A | 11/1999 | Chinn |
| 6,007,497 A | 12/1999 | Huitema |
| 6,069,748 A | 5/2000 | Bietry |
| 6,086,544 A | 7/2000 | Hibner et al. |
| 6,102,866 A | 8/2000 | Nields et al. |
| 6,203,498 B1 | 3/2001 | Bunce et al. |
| 6,273,862 B1 | 8/2001 | Privitera et al. |
| 6,364,839 B1 | 4/2002 | Little et al. |
| D461,895 S | 8/2002 | Barnes et al. |
| 6,428,487 B1 | 8/2002 | Burdorff et al. |
| 6,471,651 B1 | 10/2002 | Hwang et al. |
| 6,582,368 B2 | 6/2003 | Holdaway et al. |
| 6,605,095 B2 | 8/2003 | Grossman |
| 6,688,758 B2 | 2/2004 | Thibault |
| 6,689,067 B2 | 2/2004 | Sauer et al. |
| 6,692,200 B2 | 2/2004 | Peterson |
| 6,702,749 B2 | 3/2004 | Paladini et al. |
| 6,752,768 B2 | 6/2004 | Burdorff et al. |
| 6,945,942 B2 | 9/2005 | Van Bladel et al. |
| 7,024,791 B2 | 4/2006 | Marshall et al. |
| 7,031,367 B2 | 4/2006 | Marshall et al. |
| 7,041,058 B2 | 5/2006 | Piehler |
| 7,269,907 B2 | 9/2007 | Levine et al. |
| 7,303,530 B2 | 12/2007 | Barnes et al. |
| 7,310,887 B2 | 12/2007 | Nash et al. |
| 7,367,945 B2 | 5/2008 | Dasgupta et al. |
| 7,416,533 B2 | 8/2008 | Gellman et al. |
| 7,722,549 B2 | 5/2010 | Nakao |
| 7,858,038 B2 | 12/2010 | Andreyko et al. |
| 8,162,852 B2 | 4/2012 | Norris |
| 2002/0173719 A1 | 11/2002 | Zhao et al. |
| 2003/0014010 A1 | 1/2003 | Carpenter et al. |
| 2003/0069502 A1 | 4/2003 | Makin et al. |
| 2003/0199753 A1 | 10/2003 | Hibner et al. |
| 2003/0199754 A1 | 10/2003 | Hibner et al. |
| 2003/0199785 A1 | 10/2003 | Hibner et al. |
| 2004/0034280 A1 | 2/2004 | Privitera et al. |
| 2004/0077972 A1 | 4/2004 | Tsonton et al. |
| 2004/0106934 A1 | 6/2004 | Grossman |
| 2004/0249278 A1 | 12/2004 | Krause |
| 2005/0065453 A1 | 3/2005 | Shabaz et al. |
| 2005/0131291 A1 | 6/2005 | Floyd et al. |
| 2006/0144548 A1 | 7/2006 | Beckman et al. |
| 2006/0155210 A1* | 7/2006 | Beckman ............ A61B 10/0275 600/564 |
| 2006/0200041 A1 | 9/2006 | Weikel et al. |
| 2007/0049822 A1 | 3/2007 | Bunce et al. |
| 2007/0149878 A1 | 6/2007 | Hankins |
| 2007/0167736 A1 | 7/2007 | Dietz et al. |
| 2007/0232953 A1 | 10/2007 | Dietz et al. |
| 2008/0015429 A1 | 1/2008 | Tsonton et al. |
| 2008/0146915 A1 | 6/2008 | McMorrow |
| 2009/0171218 A1 | 7/2009 | Nygaard et al. |
| 2009/0326412 A1 | 12/2009 | Pakter |
| 2010/0174185 A1 | 7/2010 | Wang et al. |
| 2011/0087132 A1 | 4/2011 | DeFreitas et al. |
| 2011/0125055 A1 | 5/2011 | Privitera et al. |
| 2011/0319759 A1 | 12/2011 | Liu et al. |
| 2012/0265097 A1* | 10/2012 | Melchiorri ......... A61B 10/0266 600/567 |
| 2013/0223590 A1 | 8/2013 | Rafaeli et al. |
| 2016/0256137 A1* | 9/2016 | Snow ................ A61B 10/0233 |
| 2017/0231607 A1* | 8/2017 | Imai .................. A61B 10/0275 600/567 |
| 2017/0303889 A1* | 10/2017 | Grim ................ A61B 10/0266 |
| 2018/0035914 A1 | 2/2018 | Fullerton et al. |
| 2018/0103939 A1* | 4/2018 | Van Liere .......... A61B 10/0283 |
| 2018/0140279 A1* | 5/2018 | Perrey ................ A61B 8/5223 |
| 2018/0280053 A1* | 10/2018 | Coker .................... A61B 8/466 |
| 2018/0333147 A1 | 11/2018 | Snow et al. |
| 2020/0187981 A1* | 6/2020 | Tian .................... A61B 8/0841 |
| 2021/0000553 A1* | 1/2021 | St. Pierre .............. A61B 34/25 |

FOREIGN PATENT DOCUMENTS

| | | |
|---|---|---|
| WO | 2008120137 A1 | 10/2008 |
| WO | 2009067740 A1 | 6/2009 |
| WO | 2015193917 A2 | 12/2015 |

OTHER PUBLICATIONS

International Search Report and Written Opinion dated Jul. 14, 2020, issued in corresponding international application No. PCT/US2020/025673, 8 pages.

* cited by examiner

BIOPSY DEVICES AND METHODS OF USE THEREOF

BACKGROUND

Technical Field

The present disclosure relates to biopsy sampling and, more particularly, to biopsy systems, ultrasound devices thereof, and methods for navigating a biopsy needle to a target location using the ultrasound device.

Description of Related Art

To have the best chance of successfully treating cancer, it is critical to diagnose cancer at an early stage. Various methods are used to identify the existence of abnormalities in tissue prior to a patient being symptomatic. For example, women regularly go for prophylactic mammograms to determine whether there are any early stage tumors developing in their breast tissue. Although mammography is effective at identifying whether a tumor is present, mammography is not capable of differentiating between benign and malignant tumors. Accordingly, upon identifying an abnormality in the tissue, the status of the abnormality needs to be determined using an additional diagnostic technique.

One method to verify whether a tissue is cancerous is to obtain a tissue sample for histological examination through a biopsy of the tissue (e.g., breast tissue) near the lesion. There are a number of devices and methods for performing a biopsy. In some instances, a tumor may be identified using manual palpation of the breast tissue and then a biopsy needle may be positioned over the identified tumor to take a sample of tissue. Another method involves holding an ultrasound probe in one hand while holding the biopsy needle with a second hand and guiding the biopsy needle along the image plane of the ultrasound probe.

SUMMARY

Provided in accordance with the disclosure is a biopsy device including an elongated handle body having a proximal end portion and a distal end portion, a needle disposed within the handle body and configured to move between a retracted position and a deployed position, and first and second ultrasound transducers disposed within the distal end portion of the handle body. The first and second ultrasound transducers define a space therebetween configured for passage of the needle. The first and second ultrasound transducers are angled relative to one another.

In aspects, the biopsy device may further include a display coupled to the proximal end portion of the handle body. The first and second ultrasound transducers may be in operable communication with the display to enable display of an ultrasound image generated by the first and second ultrasound transducers on the display.

In aspects, the first ultrasound transducer may have a distally-oriented surface defining a first plane, and the second ultrasound transducer may have a distally-oriented surface defining a second plane. The first and second planes may be disposed relative to one another at an angle of between 80 degrees and 170 degrees.

In aspects, the angle between the first and second planes may be between 140 degrees and 165 degrees.

In aspects, the biopsy device may further include a needle cartridge, a cannula cartridge, and a cutting cannula. The needle cartridge may be movably supported in the handle body and biased in a distal direction relative to the handle body. The needle may extend distally from the needle cartridge. The cannula cartridge may be movably supported in the needle cartridge and biased in the distal direction relative to the needle cartridge. The cutting cannula may extend distally from the cannula cartridge. The needle may be slidably received in the cutting cannula.

In aspects, the needle cartridge may be axially movable relative to the handle body between a retracted position and a deployed position. In the retracted position, a distal tip of the needle is disposed within the handle body, and in the deployed position, the distal tip extends distally beyond the distal end portion of the handle body.

In aspects, the cutting cannula may be axially movable relative to the needle between a retracted position and a deployed position. In the retracted position, the cutting cannula is disposed within the handle body, and in the deployed position, the cutting cannula is disposed over the distal tip of the needle and extends distally beyond the distal end portion of the handle body.

In aspects, the needle cartridge may be configured to advance the needle and the cutting cannula together as the needle moves from the retracted position to the deployed position. The cannula cartridge may be configured to advance the cutting cannula relative to the needle from the retracted position to the deployed position after advancement of the needle a selected distance.

In aspects, the cannula cartridge may have a flexible arm supported on a ledge of the needle cartridge for maintaining the cutting cannula in a retracted position relative to the needle. The arm may be configured to disengage the ledge of the needle cartridge upon the needle advancing a selected distance to allow the cutting cannula to advance relative to the needle.

In aspects, the handle body may have a tapered inner surface configured to engage and inwardly flex the arm out of engagement with the ledge upon the needle moving to the deployed position. As such, a distally-oriented bias on the cannula cartridge may urge the cannula cartridge and the cutting cannula toward a deployed position.

In aspects, the biopsy device may further include proximal and distal carriages and a first biasing member. The proximal carriage may be disposed within the handle body and movable between a proximal position and a distal position. The distal carriage may be disposed distally of the proximal carriage and movable between a proximal position and a distal position. The first biasing member may be disposed between the proximal carriage and the needle cartridge. The first biasing member may distally bias the needle cartridge relative to the proximal carriage.

In aspects, the biopsy device may further include a proximal stop and a distal stop. The proximal stop may be configured to selectively hold the proximal carriage in the distal position, and the distal stop may be configured to selectively hold the distal carriage in the proximal position. In the proximal position, the first biasing member may be compressed between the proximal and distal carriages.

In aspects, the first biasing member may be configured to advance the needle and the cutting cannula together in response to the distal stop releasing the distal carriage.

In aspects, the biopsy device may further include a second biasing member disposed between the needle cartridge and the cannula cartridge. The second biasing member may distally bias the cutting cannula relative to the needle.

In aspects, the cannula cartridge may be configured to move between a retracted position, in which a distal tip of the cutting cannula is disposed proximally of a distal tip of the needle, and a deployed position, in which the distal tip of the cutting cannula overlaps with the distal tip of the needle.

In aspects, the cannula cartridge may be held in the retracted position until the needle is advanced a selected distance.

In aspects, the biopsy device may further include a third biasing member disposed between the needle cartridge and a support surface in the distal end portion of the handle body. The third biasing member may be configured to automatically retract the needle and the cutting cannula together upon the cutting cannula moving to the deployed position.

In aspects, the biopsy device may further include a plunger and an activation trigger. The plunger may extend proximally from the proximal end portion of the handle body. The plunger may be configured to be manually advanced to compress the first biasing member between the proximal and distal carriages to arm the biopsy device. The activation trigger may be movably coupled to the handle body and operably coupled to the distal stop for manually releasing the distal stop from the distal carriage to activate the biopsy device.

In accordance with another aspect of the disclosure, a biopsy device is provided and includes an elongated handle body having a proximal end portion and a distal end portion, a needle cartridge disposed within the handle body, a needle extending distally from the needle cartridge, a cannula cartridge, a cutting cannula, first and second ultrasound transducers, and a display. The needle is configured to move with the needle cartridge between a retracted position, in which a distal tip of the needle is received in the handle body, and a deployed position in which the distal tip of the needle extends distally of the handle body. The cannula cartridge is supported in the needle cartridge and configured to move relative to the needle cartridge. The cutting cannula extends distally from the cannula cartridge and is disposed over the needle. The cutting cannula is configured to move distally relative to the needle from a retracted position, in which a distal tip of the cutting cannula is disposed proximally of the distal tip of the needle, to a deployed position. The cutting cannula moves to the deployed position after the needle cartridge, the needle, the cannula cartridge, and the cutting cannula advance together a selected distance. The first and second ultrasound transducers are disposed within the distal end portion of the handle body. The first and second ultrasound transducers define a space therebetween configured for passage of the needle and the cutting cannula. The first and second ultrasound transducers are angled relative to one another. The display is coupled to the proximal end portion of the handle body. The first and second ultrasound transducers are in communication with the display and configured to send a signal to the display to generate an image on the display.

In aspects, the distal tip may have a beveled edge defining a plane. The needle may be oriented such that the plane of the beveled edge is perpendicular relative to an imaging plane defined by the first and second ultrasound transducers.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Various aspects and features of the present disclosure are described hereinbelow with references to the drawings, wherein.

DETAILED DESCRIPTION

Biopsy devices, biopsy systems, and methods for navigating the biopsy devices to a target location and obtaining a tissue sample using the biopsy device are provided in accordance with the present disclosure and described in detail below. In one embodiment, the biopsy device includes a handle assembly in the form of an ultrasound probe, and a needle coupled to the handle assembly and configured for penetrating and extracting tissue from a lesion. The handle assembly has a display for illustrating both a needle tip of the needle and the target tissue such that the needle can be accurately navigated into the targeted portion of the lesion. The ultrasound probe has a pair of ultrasound transducers that are laterally spaced from one another to allow for passage of the needle therebetween. The ultrasound transducers are angled toward a path of the needle to provide for improved imaging of the needle and the targeted portion of the lesion.

Figure 1:
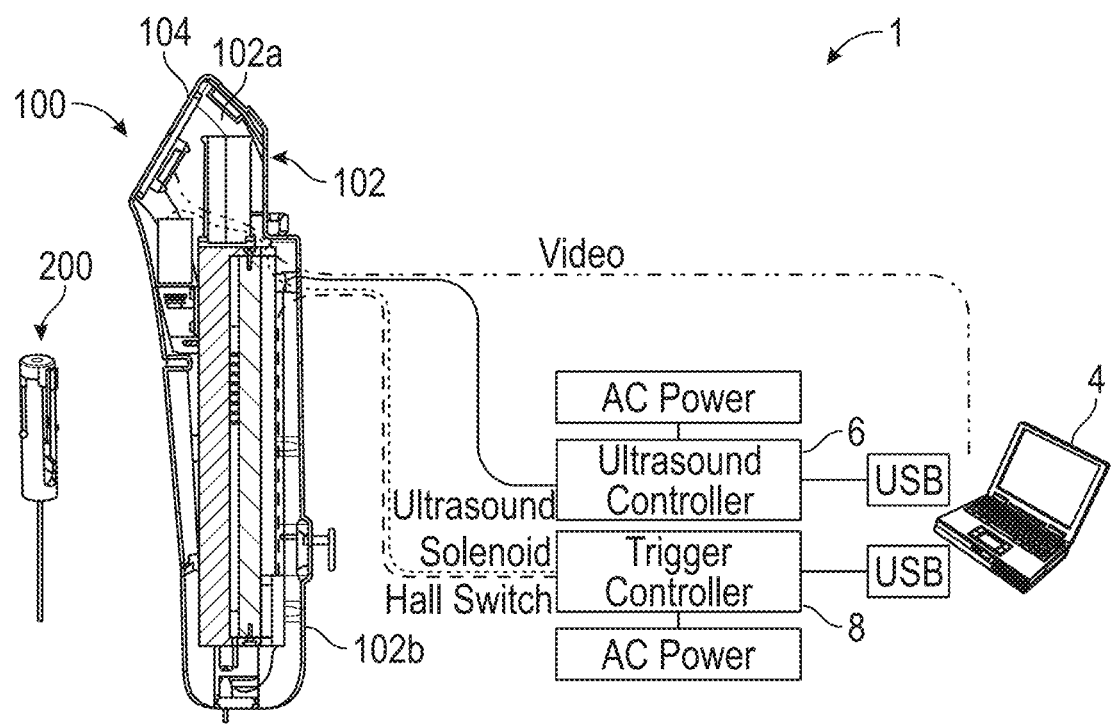
FIG. 1 is a schematic illustration of an ultrasound tissue biopsy system provided in accordance with the present disclosure configured for navigation to a target location and for obtaining a tissue sample.
Figure 2:
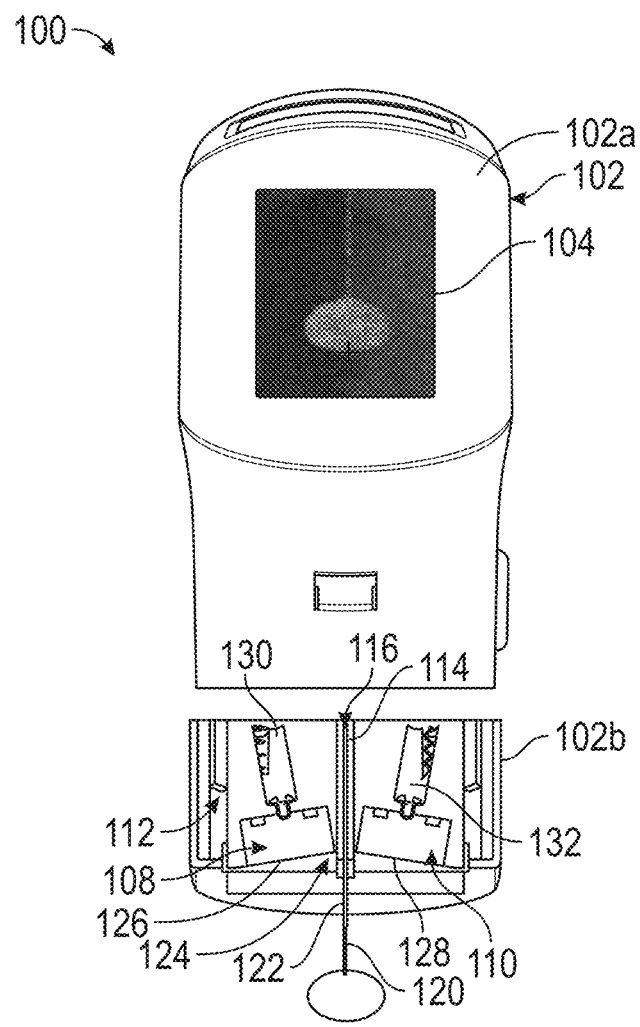
FIG. 2 is a plan view, with parts removed, illustrating a biopsy device of the system of FIG. 1 including angled first and second ultrasound transducers.
Figure 3:
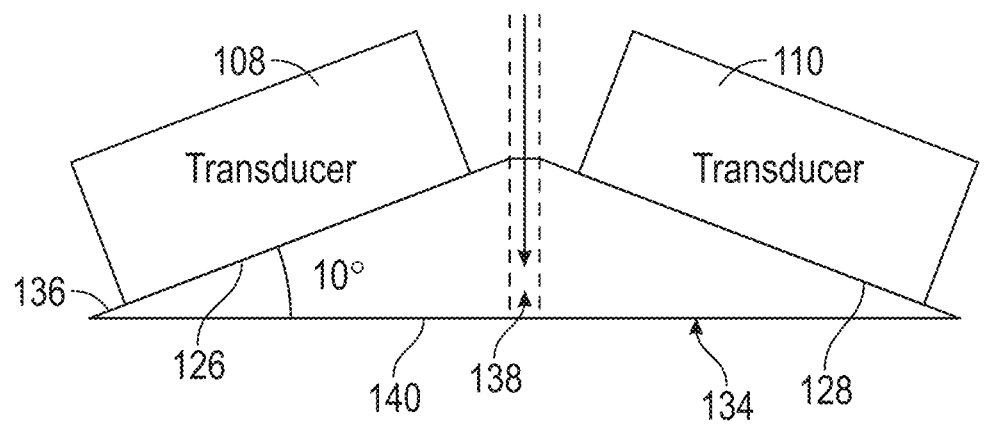
FIG. 3 is a side cross-sectional view illustrating the first and second ultrasound transducers of FIG. 2 interfacing with a coupling wedge.

With reference to FIGS. 1-3, an ultrasound tissue biopsy system 1 is provided in accordance with the present disclosure for obtaining a tissue sample from a target tissue, for example, a lesion. The ultrasound tissue biopsy system 1 generally includes a biopsy device 100 incorporating a core needle assembly 200 and a control device 4 (e.g., a computer) interfacing with the biopsy device 100. The biopsy device 100 generally includes an elongated handle body 102, a display 104 supported in a proximal end portion 102a of the handle body 102, and first and second ultrasound transducers 108, 110 supported in a distal end portion 102b of the handle body 102.

The ultrasound transducers 108, 110 are configured to send ultrasound waves toward a selected tissue site, whereby the tissue site, based upon its physical characteristics, reflects ultrasound waves back to the ultrasound transducers 108, 110, which detect the reflected ultrasound waves and send corresponding signals to a central processing unit (not shown) of the biopsy device 100. In some aspects, the central processing unit may be incorporated into the control device 4. The central processing unit is configured to generate an image on the display 104 based upon the signals received from each of the ultrasound transducers 108, 110 by combining the two separate 2D ultrasound images from the ultrasound transducers 108, 110.

The handle body 102 may be fabricated from plastic, such as, for example, PEEK, and defines a hollow interior 112 therein for housing various components of the biopsy device 100. Other suitable materials from which the handle body 102 is formed are contemplated. The handle body 102 may be received in a sterile, disposable cover (not shown). The disposable cover may extend into the handle body 102 to provide a barrier between the handle body 102 and the core needle assembly 200. The handle body 102 may house a memory (e.g., an EEPROM—not shown) for storing a variety of information regarding the biopsy device 100. In embodiments, the memory is additionally or alternatively associated with the control device 100.

The distal end portion 102b of the handle body 102 houses a molded support block 114 therein. The support block 114 defines a longitudinally-extending channel 116 therethrough configured for passage of a needle 120 and a cutting cannula 122 of the core needle assembly 200. The ultrasound transducers 108, 110 may be molded into pockets formed in the support block 114. The ultrasound transducers 108, 110 are set within the support block 114 at an angle relative to one another and laterally spaced from one another to define a space 124 therebetween. As such, the channel 116 of the support block 114 extends between the first and second ultrasound transducers 108, 110, whereby the angled configuration of the first and second ultrasound transducers 108, 110 orients the transducers 108, 110 toward a longitudinal axis defined by the channel 116.

More specifically, each of the first and second ultrasound transducers 108, 110 has a distally-oriented, planar base surface 126, 128 that transmits ultrasound waves therefrom. The base surface 126 of the first transducer 108 defines a plane, and the base surface 128 of the second transducer 110 defines a plane that intersects the plane of the first transducer 108 at an angle of between about 80 degrees and about 170 degrees (wherein "about" takes into account generally accepted tolerances, e.g., material, manufacturing, environmental, measurement, and use tolerances). In embodiments, the angle between the base surfaces 126, 128 may be between about 140 degrees and about 170 degrees, and in some embodiments, about 160 degrees. Each of the transducers 108, 110 has a cable 130, 132 such as, for example, a flex circuit extending therefrom that electrically connects to the central processing unit for transmitting electrical signals (e.g., electrical signals representing 2D images) to the central processing unit to enable display of an image on display 104 and/or to an ultrasound controller 6 (FIG. 1).

The biopsy device 100 includes a coupling wedge 134 (FIG. 3) interfacing with the base surfaces 126, 128 of the ultrasound transducers 108, 110. Due to the first and second transducers 108, 110 being angled relative to one another and facing the longitudinal axis of the channel 116 of the support block 114, the coupling wedge 134 has a substantially triangular configuration. The coupling wedge 134 is fabricated from an acoustically-transparent material, such as, for example, PEEK, silicone, polyurethane, etc., and has an upper surface 136 that complementarily engages the base surfaces 126, 128 of the respective ultrasound transducers 108, 110. The coupling wedge 134 closes a gap between the bottom surface 126, 128 of the transducers 108, 110 and a skin surface of a patient during use, thereby facilitating the transmission of ultrasound waves from the transducers 108, 110 into tissue.

The coupling wedge 134 defines a channel 138 through a central portion thereof configured for passage of the needle 120 and cutting cannula 122. The channel 138 of the coupling wedge 134 is coaxial with the channel 116 of the support block 114 to allow for the passage of the needle 120 and cutting cannula 122 through the support block 114, the coupling wedge 134, and into tissue. The coupling wedge 134 has a planar, base surface 140 configured to be oriented toward tissue. The base surface 126, 128 of each of the first and second ultrasound transducers 108, 110 is disposed at an acute angle relative to the base surface 140 of the coupling wedge 134. In aspects, the acute angle may be between about 5 degrees and about 20 degrees, and in some embodiments, about 10 degrees. The coupling wedge 134 may be fabricated and subsequently affixed to the transducers 108, 110 or may be molded around the transducers 108, 110.

With reference to FIGS. 4A-6D, the core needle assembly 200 of the biopsy device 100 and components for deploying the core needle assembly 200 are now described. The core needle assembly 200 generally includes a needle cartridge 202 and a cannula cartridge 204 movably supported in the needle cartridge 202. The needle 120 is supported by and extends distally from the needle cartridge 202, and the cutting cannula 122 is supported by and extends distally from the cannula cartridge 204.

Figure 4A:
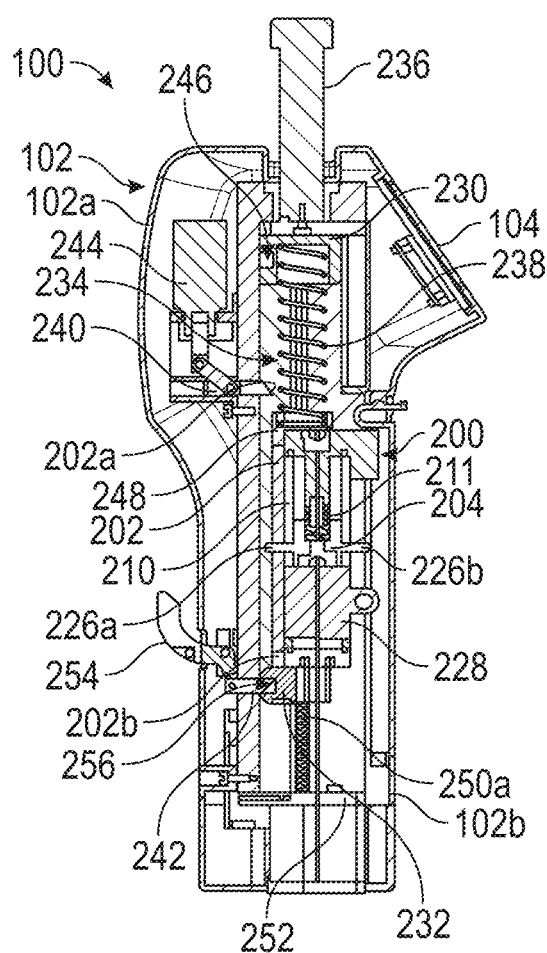
FIGS. 4A and 4B are respective side and front cross-sectional views illustrating the biopsy device of FIG. 2 in a starting condition.
Figure 4B:
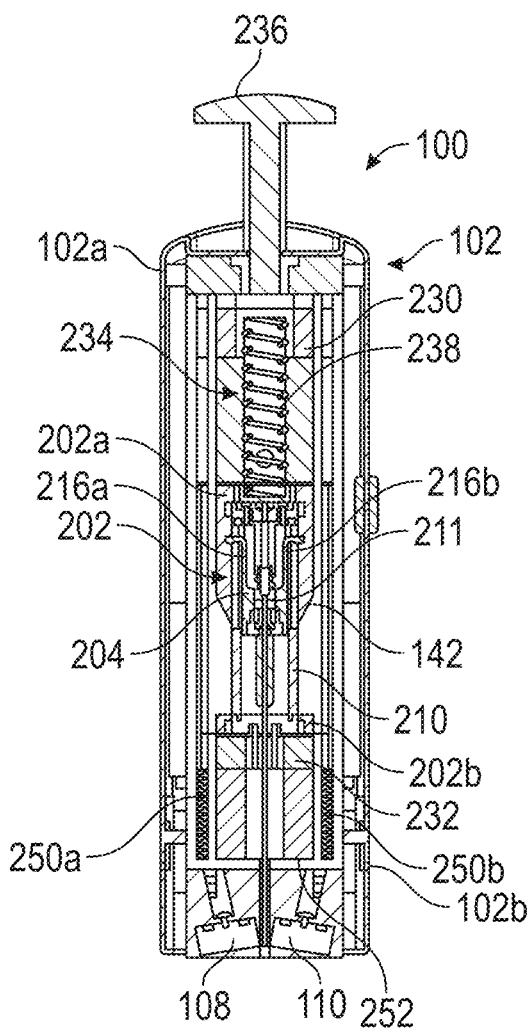
Figure 5:
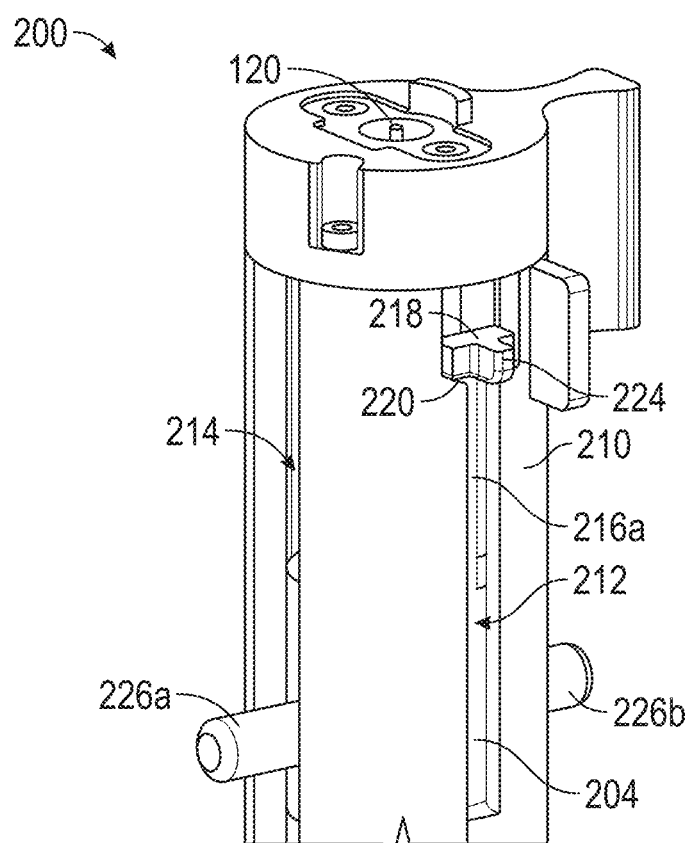
FIG. 5 is a perspective view illustrating a needle cartridge of the biopsy device of FIG. 2 housing a cannula cartridge.
Figure 6A:
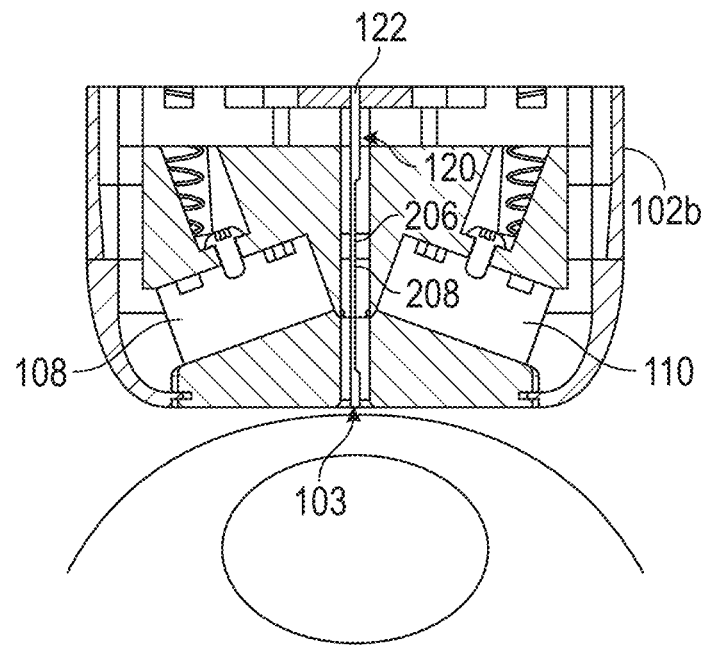
FIGS. 6A-6D are side cross-sectional views of a distal end portion of the biopsy device of FIG. 2 illustrating progressive stages of deployment of a core needle assembly.

In a starting condition of the biopsy device 100, as shown in FIGS. 4A, 4B, and 6A, a distal tip 206 of the needle 120 is disposed within the distal end portion 102b of the handle body 102 and between the ultrasound transducers 108, 110 in close proximity to an exit opening 103 in the handle body 102. The needle 120 is a side-biting needle defining an elongate cutout 208 in the distal tip 206 configured to receive a sample of tissue therein. In some embodiments, the needle 120 may be a center coring needle or define another suitable configuration. The needle 120 may be echogenically-enhanced to be more visible with ultrasound. For example, the distal tip 206 of the needle 120 may have surface features that are etched (e.g., sandblasted) into the outer surface of the distal tip 206. The surface features may be grooves, notches, or the like.

The needle cartridge 202 includes a hollow cylindrical body 210 slidably supported in the handle body 102. The cylindrical body 210 defines a first pair of longitudinally-extending slots 212 along an outer surface thereof, and a second pair of longitudinally-extending slots 214 along the outer surface thereof (only one of each of slots 212 and 214 is explicitly shown). The cylindrical body 210 defines a ledge 220 disposed at a proximal end of the slot 212 for supporting the cannula cartridge 204 in a retracted position, as will be described.

Figure 6B:
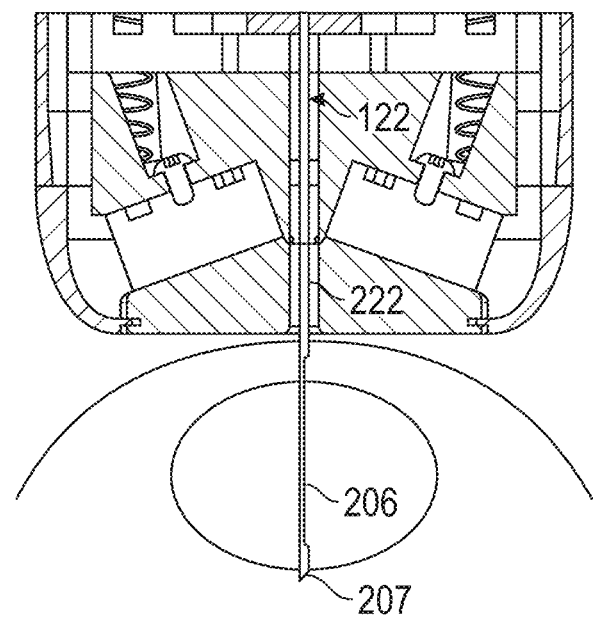

The cannula cartridge 204 is slidably received in the cylindrical body 210 of the needle cartridge 202. A biasing member 211 is disposed within the cylindrical body 210 and between a proximal end portion 202a of the needle cartridge 202 and the cannula cartridge 204. The cannula cartridge 204 has a pair of flexible arms 216a, 216b that extend out of the cylindrical body 210 through the respective first pair of slots 212. Each of the flexible arms 216a, 216b has a T-shaped end 218 (FIG. 5) supported on the ledge 220 of the cylindrical body 210. The ledge 220 of the cylindrical body 210 maintains the cannula cartridge 204 in the retracted position relative to the needle cartridge 202, in which a distal tip 222 of the cutting cannula 122 is spaced proximally from the distal tip 206 of the needle, as shown in FIGS. 6A and 6B.

Figure 8A:
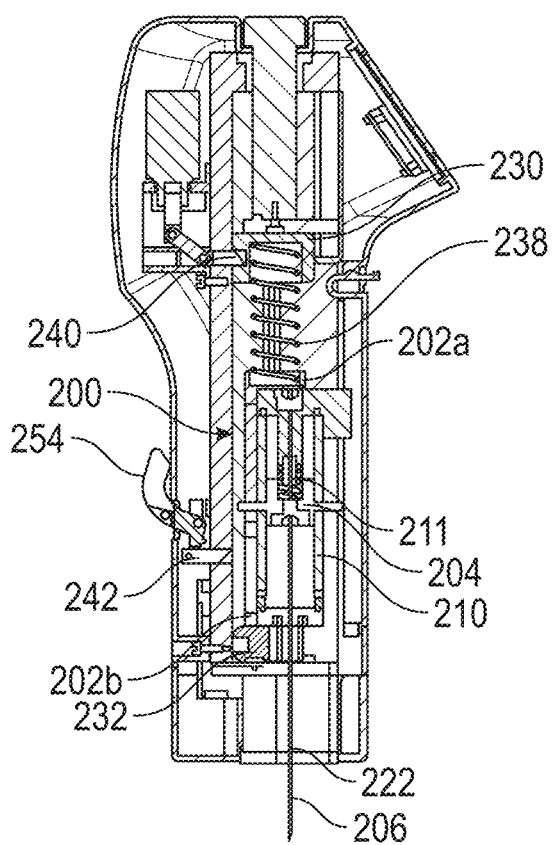
FIGS. 8A and 8B are respective side and front cross-sectional views of the biopsy device of FIG. 2 illustrating the needle in a deployed position.
Figure 8B:
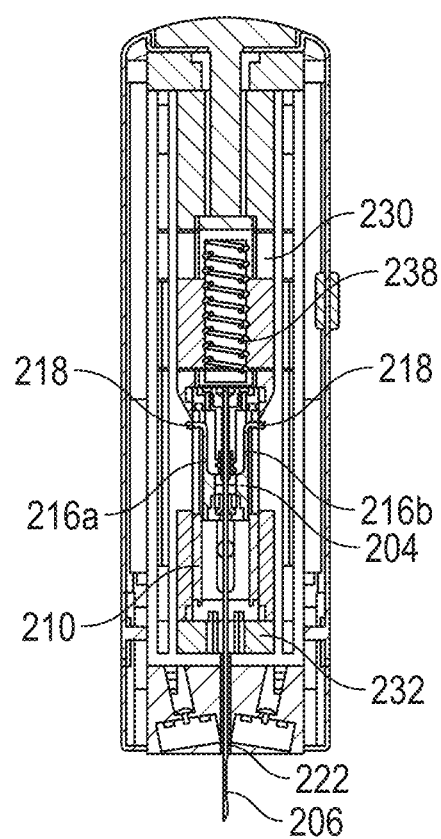
Figures 9A, 9B:
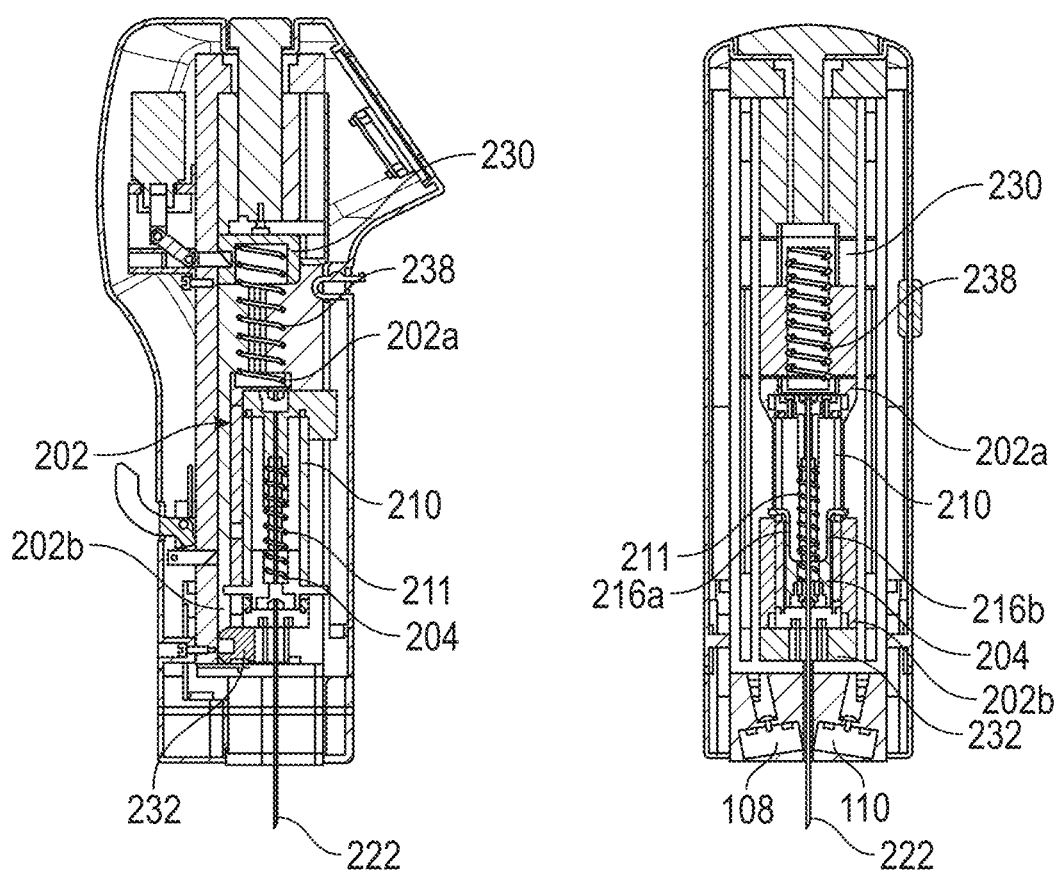
FIGS. 9A and 9B are respective side and front cross-sectional views of the biopsy device of FIG. 2 illustrating the cutting cannula in a deployed position.
Figure 10A:
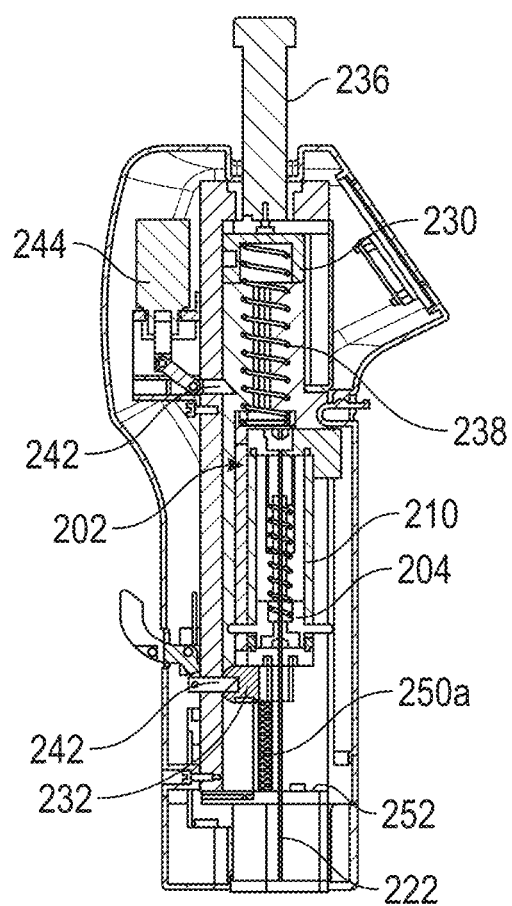
FIGS. 10A and 10B are respective side and front cross-sectional views of the biopsy device of FIG. 2 illustrating the core needle assembly in a retracted position.
Figure 10B:
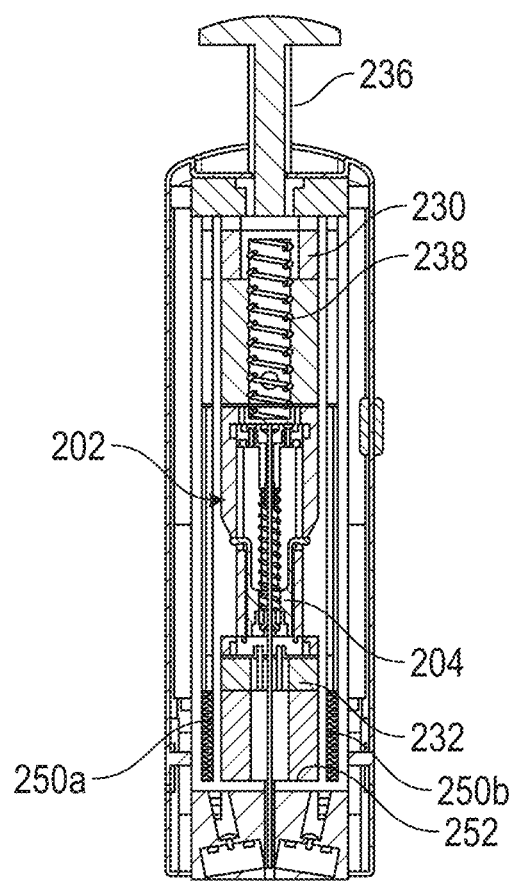

The T-shaped ends 218 of the flexible arms 216a, 216b each have a protrusion 224 disposed radially outward of the respective slot 212 of the cylindrical body 210. The protrusion 224 of each of the T-shaped ends 218 is configured to engage an inner surface 142 of the handle body 102 after the needle cartridge 202 advances toward a deployed position, as shown in FIGS. 6B, 8A, and 8B. The inner surface 142 tapers inwardly in a distal direction, such that upon the T-shaped ends 218 engaging the inner surface 142, the flexible arms 216a, 216b of the cartridge cannula 204 flex inwardly to disengage the T-shaped ends 218 from the supporting ledge 220 of the cylindrical body 210. As such, the distally-oriented bias of the biasing member 211 may then distally urge the cannula cartridge 204 and the attached cutting cannula 122 relative to the needle cartridge 202 toward a deployed position.

Figure 6C:
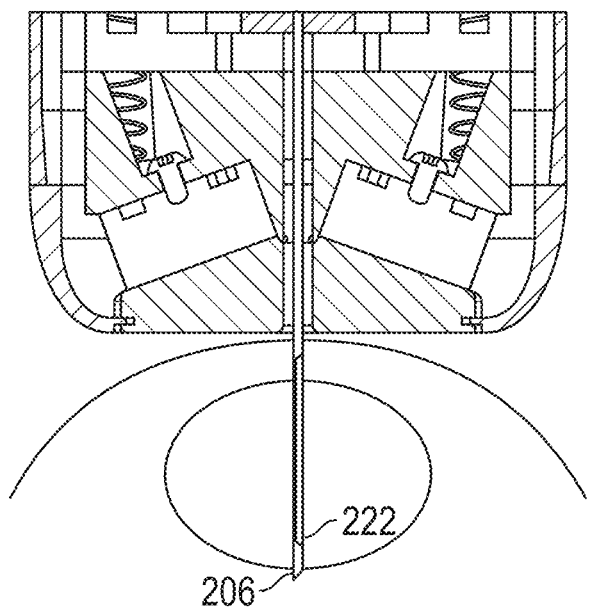
Figure 6D:
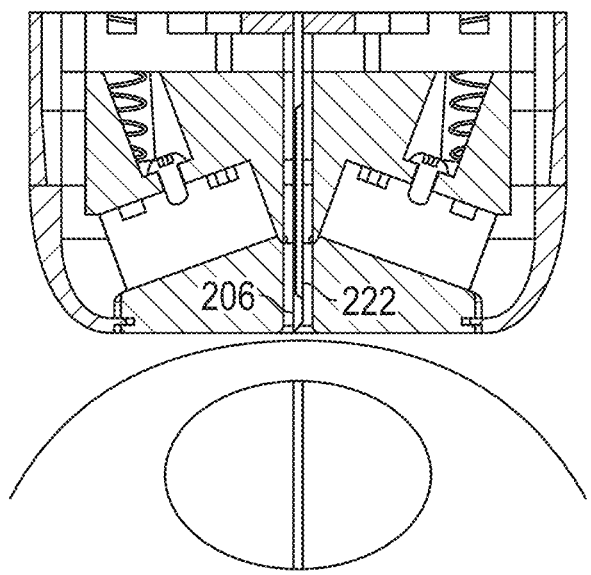

The cannula cartridge 204 may include a pair of rigid arms 226a, 226b extending transversely through the second pair of slots 214 in the cylindrical body 210. The rigid arms 226a, 226b may be used to manually retract the cannula cartridge 204 toward the retracted position. The needle core assembly 200 may be shipped with the cutting cannula 122 in the deployed position, as shown in FIGS. 6C and 6D, in which the distal tip 222 of the cutting cannula 122 covers the distal tip 206 of the needle 120. In this way, the distal tip 206 of the needle 120 will be concealed to prevent an accidental piercing. Prior to loading the core needle assembly 200 into the handle body 102, a clinician may grasp the rigid arms 226a, 226b to move the cannula cartridge 204 into the retracted position, thereby loading the biasing member 211. A safety plug 228 may be coupled to the needle cartridge 202 to maintain the cannula cartridge 204 in the retracted position while loading the needle core assembly 200 into the handle body 102. After loading the needle core assembly 200 into the handle body 102, the safety plug 228 may be removed.

With reference to FIGS. 4A, 4B, 7A, and 7B, the core needle assembly 200 is movably supported in the handle body 102 between a proximal carriage 230 and a distal carriage 232. The proximal and distal carriages 230, 232 and a biasing member 238 (e.g., a coil spring) function together to control a deployment of the needle core assembly 200. The proximal carriage 230 is slidably received in a longitudinally-extending channel 234 in the proximal end portion 102a of the handle body 102. A plunger 236 is coupled to the proximal carriage 230 and extends proximally therefrom and out of an opening in the proximal end portion 102a of the handle body 102 for access by a clinician. The biasing member 238 is disposed between the proximal carriage 230 and the proximal end portion 202a of the needle cartridge 202. A distal translation of the plunger 236 advances the proximal carriage 230 toward the needle cartridge 202, thereby compressing the biasing member 238 to arm the biopsy device 100.

The biopsy device 100 includes a proximal stop 240 disposed in the proximal end portion 102a of the handle body 102, and a distal stop 242 disposed in the distal end portion 102b of the handle body 102. The proximal stop 240 is operably coupled to an actuator, such as, for example, a solenoid 244, and may be configured as a sliding pin extending transversely into the channel 234 of the handle body 102. The proximal carriage 230 defines a recess 246 in a lateral side thereof configured to receive a ramped end surface 248 of the proximal stop 240 upon the proximal carriage 230 moving from a proximal, starting position, shown in FIGS. 4A and 4B, to a distal, armed position, shown in FIGS. 7A and 7B.

Upon advancing the proximal carriage 230 from the starting position to the armed position, the proximal carriage 230 engages the ramped end surface 248 of the proximal stop 240 to shift the proximal stop 240 in a first direction (e.g., to the left in FIG. 4A) out of the path of the proximal carriage 230. When the recess 246 is aligned with the proximal stop 240, the proximal stop 240 shifts in a second direction (e.g., to the right in FIG. 7A) into the recess 246 of the proximal carriage 230 to hold the proximal carriage 230 in a loaded state, in which the biasing member 238 is compressed between the proximal carriage 230 and the proximal end portion 202a of the needle cartridge 202. The solenoid 244 may be in communication (e.g., wireless or wired) with a trigger controller 8 (FIG. 1) for activating the solenoid 244 to move the proximal stop 240 out of engagement with the recess 246 of the proximal carriage 230.

The distal carriage 232 supports a distal end portion 202b of the needle cartridge 202 and is slidably received in the distal end portion 102b of the handle body 102. The distal carriage 232 is resiliently biased toward a proximal position, as shown in FIG. 4A, by a pair of retraction springs 250a, 250b disposed between the distal carriage 232 and a support surface 252 of the handle body 102. The biopsy device 100 has an activation trigger 254 pivotably coupled to the distal end portion 102b of the handle body 102 and accessible by a clinician from outside of the handle body 102. The activation trigger 254 is coupled to the distal stop 242 and is configured to slide the distal stop 242 out of engagement with a recess 256 defined in a lateral side of the distal carriage 232.

Figure 7A:
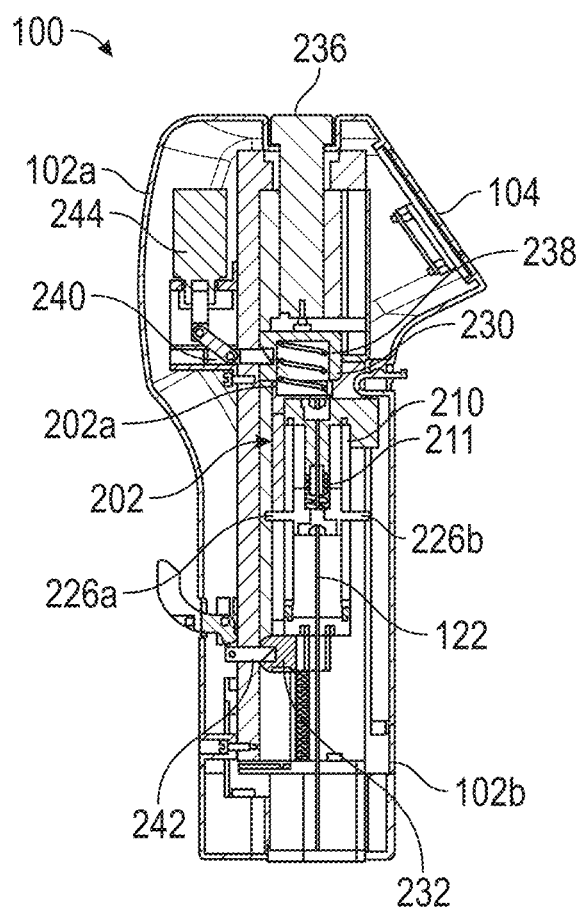
FIGS. 7A and 7B are respective side and front cross-sectional views illustrating the biopsy device of FIG. 2 in an armed, pre-fired condition.
Figure 7B:
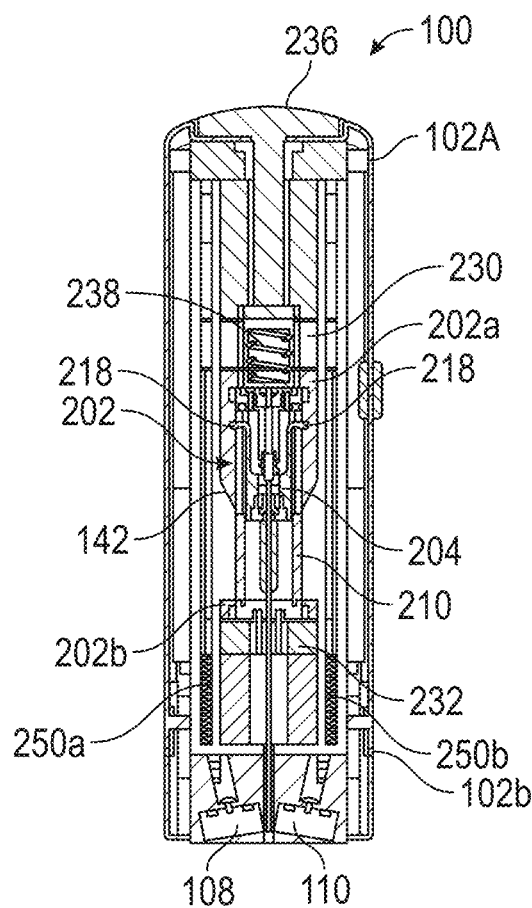

When the distal stop 242 is disposed within the recess 256 of the distal carriage 232, the distal carriage 232 is prevented from advancing from the proximal position as the proximal carriage 230 is advanced from the proximal position (FIGS. 4A and 4B) to the distal position (FIGS. 7A and 7B). In this way, during advancement of the proximal carriage 230, the biasing member 238 is compressed between the proximal carriage 230 and the proximal end portion 202 of the needle cartridge 202 so long as the needle cartridge 202 is held in position by the distal carriage 232. With the proximal carriage 230 fixed in the distal position by the proximal stop 240, a release of the distal carriage 232 from the distal stop 242 allows the biasing member 238 to distally urge the needle cartridge 202, which carries along therewith the needle 120, the cannula cartridge 204, and the cutting cannula 122.

One use of the ultrasound tissue biopsy system 1 for extracting tissue samples from a lesion, e.g., a tumor, is described in detail with reference to FIGS. 7A-10B. The biopsy device 100 is positioned such that the distal end portion 102b of the handle body 102 is placed in abutting engagement with an outer surface of tissue (e.g., breast tissue), with the distal tip 206 of the needle 120 in proximity to target tissue, e.g., a lesion. The ultrasound transducers 108, 110 emit ultrasound waves toward the lesion and the distal tip 206 of the needle 120. The ultrasound transducers 108, 110 then receive the reflected ultrasound waves and communicate signals corresponding to the same to the central processing unit (not shown) of the computer 4 which generates an image of the distal tip 206 of the needle 120 relative to the lesion for on the display 104. In addition, the central processing unit of the system 1 may animate a projected needle pathway on the display 104 such that a clinician can accurately predict the pathway the needle 120 will travel if actuated at the present position. The biopsy device 100 is moved to a position in which the projected needle pathway animated on the display 104 is aligned with the image of the lesion.

Upon aligning the projected needle pathway with the displayed image of the lesion on the display 104, the plunger 236 of the biopsy device 100 is actuated. With the distal carriage 232 held in the proximal position by the distal stop 242, advancement of the plunger 236 compresses the biasing member 238 between the proximal and distal carriages 230, 232, thereby arming the biopsy device 100, as shown in FIGS. 7A and 7B. To actuate the core needle assembly 200, the activation trigger 254 is actuated (e.g., pivoted) to disengage the distal stop 242 from the distal carriage 232, whereby the biasing member 238 urges the needle 120 from the retracted position (FIGS. 6A, 7A, and 7B) toward the deployed position (FIGS. 6B, 8A, and 8B) and into the lesion. Since the cannula cartridge 204 of the core needle assembly 200 is supported in the needle cartridge 202, the cannula cartridge 204 and the cutting cannula 122 advance with the needle cartridge 202 and needle 120.

With reference to FIGS. 8A and 8B, upon the needle 120 advancing to the deployed position, or any suitable advanced distance, the protrusions 224 of the flexible arms 216a, 216b of the cannula cartridge 204 engage the tapered inner surface 142 of the handle body 102, whereby the T-shaped ends 218 of the flexible arms 216a, 216b disengage the ledge 220 of the cylindrical body 220. With the flexible arms 216a, 216b of the cannula cartridge 204 no longer being supported on the ledge 220 in the retracted position, the biasing member 211 in the cylindrical body 210 urges the cutting cannula 122 axially relative to the needle 120 to the deployed position (FIGS. 9A and 9B), in which the distal tip 222 of the cutting cannula 122 is disposed over the distal tip 206 of the needle 120 and extends distally beyond the distal end portion 102b of the handle body 102. With the distal tip 222 of the cutting cannula 122 encircling the distal tip 206 of the needle 120, the sample of tissue is captured in the elongate cutout 208 in the needle 120, as shown in FIG. 6C.

During advancement of the needle 120, the distal tip 206 of the needle 120 may naturally deflect in a direction away from a beveled edge 207 (FIG. 6B) that forms the piercing edge of the distal tip 206. As such, to ensure that the distal tip 206 remains within the imaging plane of the ultrasound transducers 108, 110, the angular orientation of the needle 120 is such that a plane defined by the beveled edge 207 of the distal tip 206 is perpendicular relative to the imaging plane defined by the ultrasound transducers 108, 110. In this way, as the needle 120 is advanced through tissue, the distal tip 206 will deflect in a direction parallel with the imaging plane so as to remain visible by the ultrasound transducers 108, 110 as opposed to deflecting outside of the imaging plane.

Upon advancing the cutting cannula 122 to the deployed position, the solenoid 244 may be configured to automatically retract the proximal stop 240 to release the proximal carriage 230 from the proximal stop 240. Releasing the proximal carriage 230 from the proximal stop 240 allows the retraction springs 250a, 250b and the biasing member 238 to retract the needle core assembly 200 out of the tissue and back into the handle body 102. In embodiments, actuation of the solenoid 244 may be delayed for a selected amount of time after deployment of the cutting cannula 122 to allow for an image capture of the needle 120 and cutting cannula 122 prior to their withdrawal from the tissue, thus allowing for visual confirmation of the capture of the tissue sample. A magnet (not explicitly shown) may be incorporated into the distal carriage 232 and positioned for sensing by a hall effect sensor (not explicitly shown) in the handle body 102 to determine when the cutting cannula 122 has entered the deployed position. Other types of sensors may be provided, and at any suitable locations of the biopsy device 100, to detect one or more stages of deployment of the needle core assembly 200.

In embodiments, the biopsy device 100 may be configured to deploy a marker or tracking device therefrom in addition to or instead of the core needle assembly 200. The marker may be a wire or rod that extends from the patient's skin or may be a small implantable device or chip. A cartridge housing with the marker may be loaded into the biopsy device 100 and deployed therefrom. In other embodiments, the core needle assembly 200 may further include a marker and a mechanism for deploying the marker simultaneously with deployment of the needle 120 and cutting cannula 122.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A biopsy device, comprising:
an elongated handle body having a proximal end portion and a distal end portion;
a needle disposed within the handle body and configured to move between a retracted position and a deployed position;
first and second ultrasound transducers disposed within the distal end portion of the handle body and defining a space between the first and second ultrasound transducers, the space configured for passage of the needle, wherein the first and second ultrasound transducers are angled relative to one another;
a needle cartridge movably supported in the handle body and biased in a distal direction relative to the handle body, the needle extending distally from the needle cartridge, wherein the needle cartridge is axially movable relative to the handle body between a retracted position, in which a distal tip of the needle is disposed within the handle body, and a deployed position, in which the distal tip extends distally beyond the distal end portion of the handle body;
a cannula cartridge movably supported in the needle cartridge and biased in the distal direction relative to the needle cartridge; and
a cutting cannula extending distally from the cannula cartridge, the needle being slidably received in the cutting cannula, the cutting cannula being axially movable relative to the needle between a retracted position, in which the cutting cannula is disposed within the handle body, and a deployed position in which the cutting cannula is disposed over the distal tip of the needle and extends distally beyond the distal end portion of the handle body, wherein the needle cartridge moving from the retracted position to the deployed position automatically causes the cutting cannula to move from the retracted position to the deployed position.

2. The biopsy device according to claim 1, further comprising a display coupled to the proximal end portion of the handle body, wherein the first and second ultrasound transducers are in operable communication with the display to enable display of an ultrasound image generated by the first and second ultrasound transducers on the display.

3. The biopsy device according to claim 1, wherein the first ultrasound transducer has a distally-oriented surface defining a first plane, and the second ultrasound transducer has a distally-oriented surface defining a second plane, the first and second planes disposed relative to one another at an angle of between 80 degrees and 170 degrees.

4. The biopsy device according to claim 1, wherein the needle cartridge is configured to advance the needle and the cutting cannula together as the needle moves from the retracted position to the deployed position.

5. The biopsy device according to claim 1, wherein the cannula cartridge has a flexible arm supported on a ledge of the needle cartridge for maintaining the cutting cannula in the retracted position relative to the needle, the arm configured to disengage the ledge of the needle cartridge upon the needle advancing a selected distance to allow the cutting cannula to advance relative to the needle.

6. The biopsy device according to claim 1, further comprising:
a proximal carriage disposed within the handle body and movable between a proximal position and a distal position;
a distal carriage disposed distally of the proximal carriage and movable between a proximal position and a distal position; and
a first spring disposed between the proximal carriage and the needle cartridge, wherein the first spring distally biases the needle cartridge relative to the proximal carriage.

7. The biopsy device according to claim 1, wherein the cannula cartridge is held in the retracted position relative to the needle cartridge until the needle is advanced a selected distance from the retracted position.

8. The biopsy device according to claim 3, wherein the angle between the first and second planes is between 140 degrees and 165 degrees.

9. The biopsy device according to claim 5, wherein the handle body has a tapered inner surface, the arm being configured to engage the tapered inner surface as the needle moves to the deployed position whereby the tapered inner surface inwardly flexes the arm out of engagement with the ledge, such that a distally-oriented bias on the cannula cartridge urges the cannula cartridge and the cutting cannula toward the deployed position.

10. The biopsy device according to claim 6, further comprising:
a proximal stop configured to selectively hold the proximal carriage in the distal position; and
a distal stop configured to selectively hold the distal carriage in the proximal position, in which the first spring biasing member is compressed between the proximal and distal carriages.

11. The biopsy device according to claim 10, wherein the first spring is configured to advance the needle and the cutting cannula together in response to the distal stop releasing the distal carriage.

12. The biopsy device according to claim 10, further comprising:

a plunger extending proximally from the proximal end portion of the handle body and configured to be manually advanced to compress the first spring between the proximal and distal carriages to arm the biopsy device; and
an activation trigger movably coupled to the handle body and operably coupled to the distal stop for manually releasing the distal stop from the distal carriage to activate the biopsy device.

13. The biopsy device according to claim 11, further comprising a second spring disposed between the needle cartridge and the cannula cartridge, wherein the second spring distally biases the cutting cannula relative to the needle.

14. The biopsy device according to claim 13, further comprising a third spring disposed between the needle cartridge and a support surface in the distal end portion of the handle body, wherein the third spring is configured to automatically retract the needle and the cutting cannula together upon the cutting cannula moving to the deployed position.

15. A biopsy device, comprising:
an elongated handle body having a proximal end portion and a distal end portion;
a needle cartridge disposed within the handle body;
a needle extending distally from the needle cartridge and configured to move with the needle cartridge between a retracted position, in which a distal tip of the needle is received in the handle body, and a deployed position in which the distal tip of the needle extends distally of the handle body;
a cannula cartridge supported in the needle cartridge and configured to move relative to the needle cartridge;
a cutting cannula extending distally from the cannula cartridge and disposed over the needle, the cutting cannula configured to move distally relative to the needle from a retracted position, in which a distal tip of the cutting cannula is disposed proximally of the distal tip of the needle, to a deployed position, after the needle cartridge, the needle, the cannula cartridge, and the cutting cannula advance together a selected distance, wherein the cutting cannula moves from the retracted position to the deployed position in response to the needle cartridge moving the selected distance;
first and second ultrasound transducers disposed within the distal end portion of the handle body and defining a space between the first and second ultrasound transducers, the space configured for passage of the needle and the cutting cannula, wherein the first and second ultrasound transducers are angled relative to one another; and
a display coupled to the proximal end portion of the handle body, wherein the first and second ultrasound transducers are in operable communication with the display to enable display of an ultrasound image generated by the first and second ultrasound transducers on the display.

16. The biopsy device according to claim 15, wherein the first ultrasound transducer has a distally-oriented surface defining a first plane, and the second ultrasound transducer has a distally-oriented surface defining a second plane, the first and second planes disposed relative to one another at an angle of between 80 degrees and 170 degrees.

17. The biopsy device according to claim 15, wherein the distal tip of the needle has a beveled edge defining a plane, the needle being oriented such that the plane of the beveled edge is perpendicular relative to an imaging plane defined by the first and second ultrasound transducers.

18. The biopsy device according to claim 16, wherein the angle between the first and second planes is between 140 degrees and 165 degrees.

\* \* \* \* \*